United States Patent [19]
Perren et al.

[11] Patent Number: 6,019,793
[45] Date of Patent: Feb. 1, 2000

[54] SURGICAL PROSTHETIC DEVICE

[75] Inventors: Stephan M. Perren, Davos, Switzerland; Tom Higgins, Paoli, Pa.

[73] Assignee: Synthes, Paoli, Pa.

[21] Appl. No.: 09/091,350

[22] PCT Filed: Oct. 21, 1996

[86] PCT No.: PCT/EP96/04567

§ 371 Date: Jun. 17, 1998

§ 102(e) Date: Jun. 17, 1998

[87] PCT Pub. No.: WO98/17207

PCT Pub. Date: Apr. 30, 1998

[51] Int. Cl.[7] .................................................... A61F 2/44
[52] U.S. Cl. ............................................................ 623/17
[58] Field of Search ........................ 623/17, 16, 11

[56] References Cited

U.S. PATENT DOCUMENTS

| | | | |
|---|---|---|---|
| 5,062,850 | 11/1991 | MacMillan et al. | 623/17 |
| 5,116,357 | 5/1992 | Eberbach | 606/213 |
| 5,341,815 | 8/1994 | Cofone et al. | 128/749 |
| 5,586,983 | 12/1996 | Sanders et al. | 606/61 |
| 5,749,916 | 5/1998 | Richelsoph | 623/17 |
| 5,782,832 | 7/1998 | Larsen et al. | 606/61 |
| 5,787,713 | 7/1998 | Jobe | 606/69 |
| 5,888,227 | 3/1999 | Cottle | 623/17 |

FOREIGN PATENT DOCUMENTS

| | | | |
|---|---|---|---|
| 2 712 486 | 5/1995 | France . | |
| 2 722 679 | 1/1996 | France . | |
| 94 13 778 | 1/1996 | Germany . | |
| 2008851 | 3/1994 | Russian Federation | 623/17 |
| WO 92/14423 | 9/1992 | WIPO . | |
| WO 95/13757 | 5/1995 | WIPO . | |

*Primary Examiner*—David H. Willse
*Assistant Examiner*—Alvin Stewart
*Attorney, Agent, or Firm*—Pennie & Edmonds LLP

[57] ABSTRACT

The surgical prosthetic device according to the present invention is adapted for placement between two adjoining vertebrae for total or partial replacement of the disk from therebetween. The device has two plates with interior surfaces facing each other and being held at a distance by connecting means and exterior surfaces for contacting the end plates of the two adjoining vertebrae. The connecting means is made of a shape-memory alloy.

16 Claims, 2 Drawing Sheets

SURGICAL PROSTHETIC DEVICE

FIELD OF THE INVENTION

This invention relates to a surgical prosthetic device, and in particular to an invertebral implant.

BACKGROUND

It is a well-known surgical procedure to remove a damaged disc in the spine between two adjacent vertebrae of patient and to replace it by inserting into the resulting disc space one or more implants having a combined width approximating the height of the disc space. The implant must be able to maintain the space between the two adjacent vertebrae.

Implantation of the surgical prosthetic device in the intervertebral space involves a considerable invasiveness with loss of or damage of anatomical structures.

The invention as claimed aims at solving the above described problems.

SUMMARY OF THE INVENTION

The surgical prosthetic device according to the present invention is adapted for placement between two adjoining vertebrae for total or partial replacement of the disk from between the vertebrae and has two plates with: interior surfaces facing each other and held at a distance by connecting means made of a shape-memory alloy; and exterior surfaces configured and dimensioned for contacting the end plates of the two adjoining vertebrae.

Preferably, the connecting means are wires and the two plates are also made of a shape-memory alloy. The transition temperature of the shape-memory alloy is in the range of 5° C. to 30° C., preferably between 15° C. to 25° C. The shape-memory alloy can be nitinol.

In one embodiment, the two plates have a hollow cylindrical configuration with concave sides connected by the connecting means. In a preferred embodiment, the exterior profile of the device is generally circular when the device is at a temperature below the transition temperature of the shape-memory alloy and generally rectangular when the device is at a temperature above the transition temperature of the shape-memory alloy. In a further preferred embodiment, the exterior shape of the device at a temperature below the transition temperature of the shape-memory alloy is such that the device is introducible between the two adjoining vertebrae endoscopically.

The two plates can be provided with perforations for allowing bony ingrowth and teeth to provide initial stability of the device. Preferably, the two plates are closer to each other when the device is below the transition temperature of the shape-memory alloy than when the device is above the transition temperature.

The method of maintaining the space between two adjacent vertebrae of a patient after removal of the disk from between the vertebrae according to the present invention comprises the steps of inserting a spacing device made at least partially from a shape-memory alloy into the space between the two adjacent vertebrae after removal of the disk from between the two vertebrae at a temperature below the transition temperature of the shape-memory alloy; and allowing the spacing device to reach the transition temperature and a predetermined configuration suitable to its spacing function.

In one embodiment, the method further comprises the step of configuring the spacing device to have a generally circular exterior profile when the spacing device is below the transition temperature of the shape-memory alloy and to have a generally rectangular profile when the spacing device is above the transition temperature of the shape-memory alloy. In a preferred embodiment, the method further comprises the step of endoscopically introducing the spacing device into the space between the two adjacent vertebrae. For the better understanding of the invention, its operating advantages and specific objects attained by its use, reference should be had to the accompanying drawings, examples and descriptive matter in which are illustrated and described preferred embodiments of the invention.

DETAILED DESCRIPTION OF THE PREFERRED EMBODIMENTS

Figure 1:
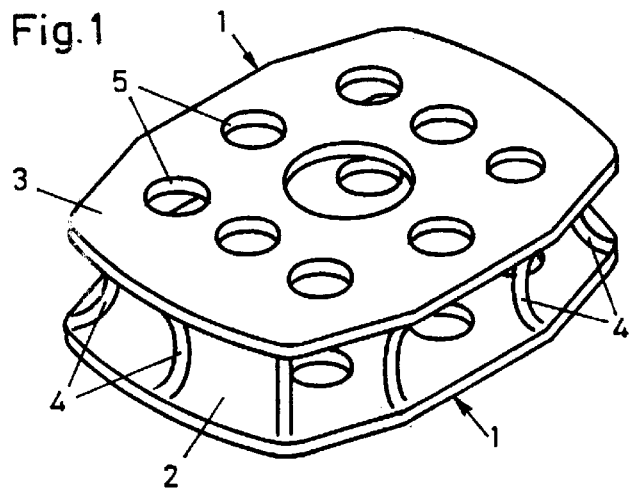
FIG. 1 is a perspective view of a device according to the invention at a temperature below the transition temperature of the memory alloy.

FIG. 1 shows a surgical prosthetic device adapted for placement between two adjoining vertebrae after removal of the disk from therebetween.

The device basically consists of two rectangular plates 1 with interior surfaces 2 facing each other and exterior surfaces 3 designed for contacting the end plates of the two adjoining vertebrae. The two plates 1 are held at a distance by connecting means 4 made of a shape-memory alloy having a transition temperature preferably in the range of 50° C.–30° C. (15° C.–25° C. being the optimal range). A range of known shape-memory alloy is suitable for the connecting means 4, i.e. nitinol. Nitinol is a nearly equal ratio of nickel and titanium which exhibits a shape-memory effect. That is, after being deformed (up to 8% strain) the material remembers its original annealed shape and will return to that original shape when heated above the shape transition temperature. In so doing, the alloy converts heat energy into mechanical work. The mechanical work done while the material is undergoing shape recovery can be much greater than that originally imparted during the initial plastic deformation. In order for an alloy to exhibit the shape-memory effect, it must be a crystalline structure which can shift into the so-called parent phase when it is subjected to a certain temperature condition and then shift into the configuration known as martensite when the temperature is lowered. The alloy is first annealed to a specified shape. The alloy may then be heated to a temperature high enough that the crystalline structure assumes the parent phase or which is referred to in the art as the austenite configuration. Next the alloy is cooled until it reverts to the martensite configuration. The alloy may now be further deformed randomly but will return to the original shape when heated to a temperature above that at which the martensite returns to the parent phase. The specific transitional temperature at which the phase transition occurs can be controlled by controlling the exact nickel to titanium ratio.

The connecting means 4 in the device according to FIG. 1 are wires or other suitable longitudinal thin elements. The geometrical configuration of the connecting elements 4 at a temperature below the transition temperature is such that the two plates 1 are held at a reduced distance compared to their distance at a temperature above the transition temperature. The connecting means 4 may be distorted in various manners as shown in FIG. 1 (bent to the inside of the device) or FIG. 2 (bent to the outside of the device).

Figure 2:
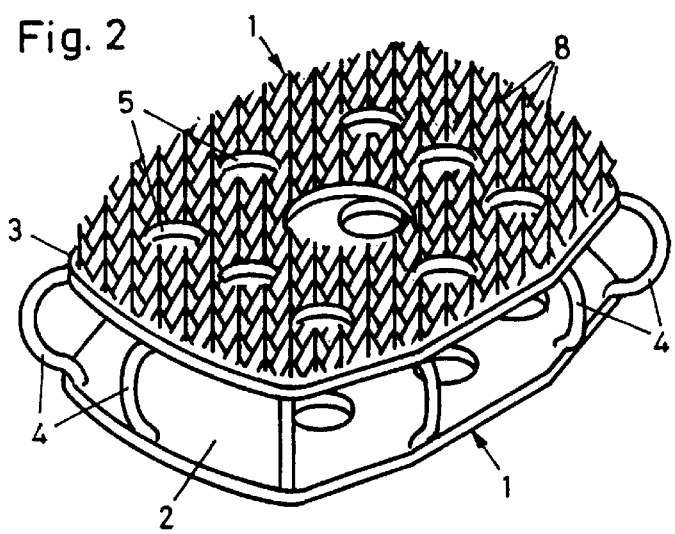
FIG. 2 is a perspective view of a modification of a device according to the invention at a temperature below the transition temperature of the memory alloy.

The embodiment shown in FIG. 2 further differs from that of FIG. 1 in that the exterior surfaces 3 of the plates 1 are provided with a three-dimensional structure 8, e.g. in the form of small teeth or pyramids.

Figure 3:
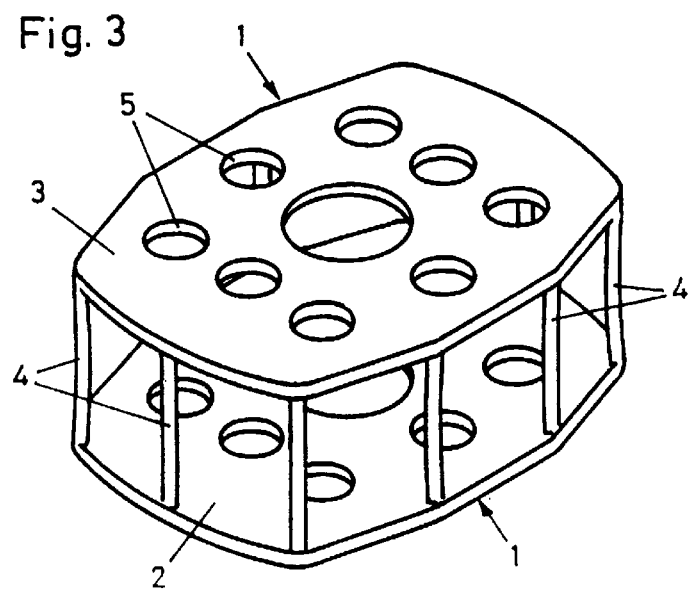
FIG. 3 is a perspective view of the device according to FIG. 1 at a temperature above the transition temperature of the memory alloy.

This distorted configuration of the connecting means 4 has the advantage that the device has a smaller volume below the transition temperature and therefore can be more easily introduced in the intervertebral space with less damage to the body tissues. After implantation of the device (held at a temperature below the transition temperature of the memory alloy, e.g. −5° C.) the body temperature (37° C.) will heat up the device to a temperature above the transition temperature of the memory alloy and the device will get into a more voluminous configuration as shown in FIG. 3 which is designed to provide optimal spacing function for the two adjacent vertebrae.

Figure 4:
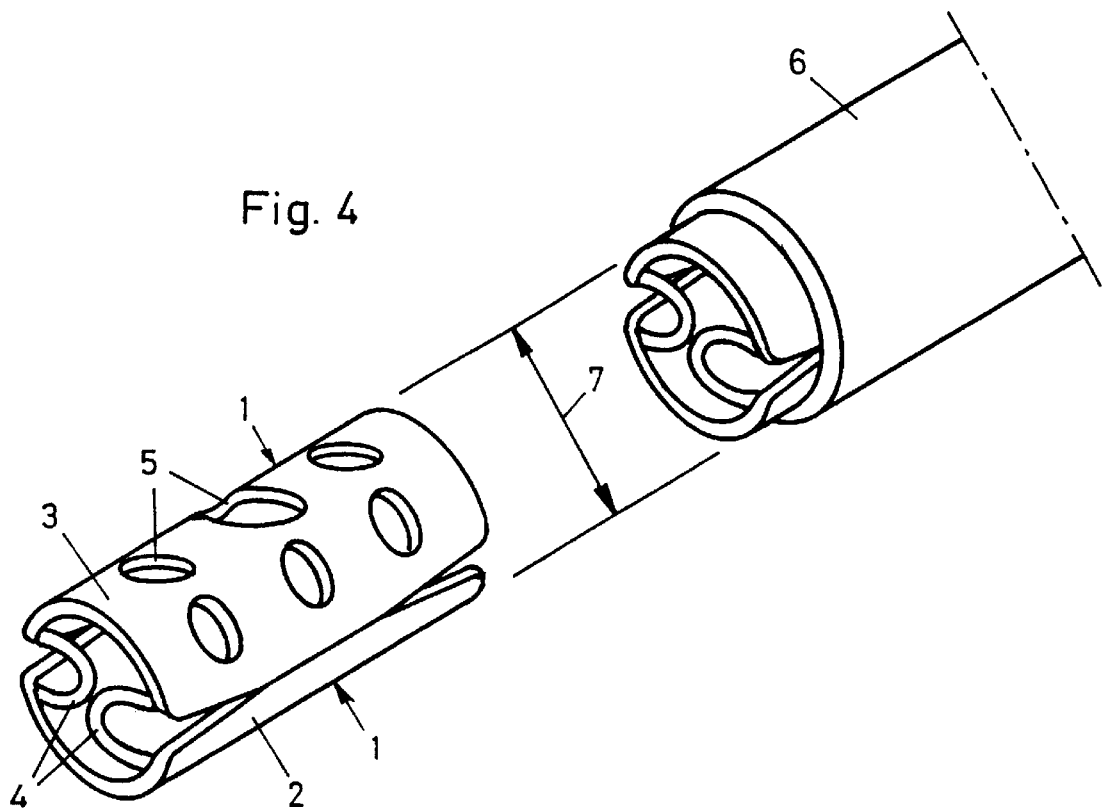
FIG. 4 is a perspective view of a modification of a device according to the invention at a temperature below the transition temperature of the memory alloy being applied by means of an endoscope.
Figure 5:
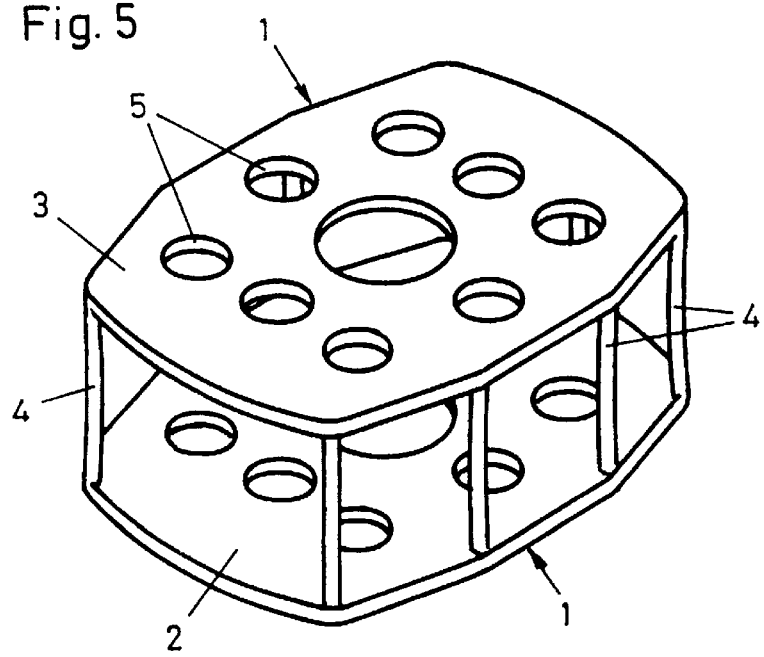
FIG. 5 is a perspective view of the device according to FIG. 4 at a temperature above the transition temperature of the memory alloy.

A preferred embodiment of the invention is shown in FIGS. 4 and 5, wherein the two plates 1 are also made of a shape-memory alloy. Preferably the two plates 1 (at a temperature below the transition temperature) have a hollow cylindrical configuration, their concave sides being connected by said connecting means 4.

As shown in FIG. 4 the shape of its exterior profile is generally circular when the device is below the transition temperature of the shape-memory alloy and generally rectangular (FIG. 5) when the device is above the transition temperature of the shape-memory alloy. This configuration of the profile of the device according to FIG. 4 allows the introduction of the device into the intervertebral space by means of an endoscope 6—as indicated in FIG. 4—having a tubular width 7 corresponding to the circular profile of the device according to FIG. 4. Typically the circular profile of the device has a diameter of approximately 20 mm.

In all embodiments of the invention the plates 1 may be provided with perforations 5 in order to facilitate bone ingrowth.

Furthermore the exterior surfaces 3 of the two plates 1 (of all embodiments) can be provided with a three-dimensional structure 8, e.g. small teeth or pyramids (FIG. 2) or similar structural elements in order to enhance fixation of the plates 1 to the end plates of the adjacent vertebrae.

The method of implanting the device according to the invention is now described referring to the embodiment according to FIG. 4 and 5.

The spacing device according to the invention is introduced into the space between two adjacent vertebrae after removal of the disk from therebetween at a temperature (e.g. 0° C.) lying below the transition temperature of the shape-memory alloy of which the device is partially or totally made. As shown in FIG. 4 introduction is best done by means of a tubular endoscope 6. After insertion the spacing device is allowed to reach transition temperature (e.g. 20° C.) and its predetermined configuration—as shown in FIG. 5—suitable to its spacing function.

While the foregoing description and drawings represent the preferred embodiments of the present invention, it will be obvious for those skilled in the art that various changes and modifications may be made therein without departing from the true spirit and scope of the present invention.

What is claimed is:

1. A surgical prosthetic device adapted for placement between two adjoining vertebrae for total or partial replacement of a disk from between the vertebrae, said device having two plates with
   interior surfaces facing each other and being held at a distance by connecting means, the distance being substantially equivalent to a height of the replaced disk; and
   exterior surfaces configured and dimensioned for contacting end plates of the two adjoining vertebrae,
   wherein the connecting means are made of a shape-memory alloy that has a transition temperature.

2. Device according to claim 1 wherein the connecting means are wires.

3. Device according to claim 1 wherein the two plates are made of a shape-memory alloy.

4. Device according to claim 1 wherein the transition temperature of the shape-memory alloy is in the range of 5° C. to 30° C.

5. Device according to claim 1 wherein the shape-memory alloy is nitinol.

6. A surgical prosthetic device adapted for placement between two adjoining vertebrae for total or partial replacement of a disk from between the vertebrae, said device having two plates with
   interior surfaces facing each other and being held at a distance by connecting means; and
   exterior surfaces configured and dimensioned for contacting end plates of the two adjoining vertebrae,
   wherein the connecting means are made of a shape-memory alloy that has a transition temperature, the two plates are made of the shape-memory alloy, and, at temperatures below the transition temperature of the shape memory alloy, the two plates of the device have a hollow cylindrical configuration with concave sides connected by said connecting means.

7. Device according to claim 6 wherein an exterior profile of the device is generally circular when the device is at a temperature below the transition temperature of the shape-memory alloy and generally rectangular when the device is at a temperature above the transition temperature of the shape-memory alloy.

8. Device according to claim 1 wherein the two plates are provided with perforations for allowing bony ingrowth.

9. Device according to claim 1 wherein exterior surfaces of said plates are provided with teeth.

10. A surgical prosthetic device adapted for placement between two adjoining vertebrae for total or partial replacement of a disk from between the vertebrae, said device having two plates with
    interior surfaces facing each other and being held at a distance by connecting means; and
    exterior surfaces configured and dimensioned for contacting end plates of the two adjoining vertebrae,
    wherein the connecting means are made of a shape-memory alloy that has a transition temperature and the two plates are closer to each other when the device is below the transition temperature of the shape-memory alloy than when the device is above the transition temperature.

11. Device according to claim 10 wherein, at a temperature below the transition temperature of the shape-memory alloy, the device has a shape which is configured and dimensioned so that the device is introducible between the two adjoining vertebrae endoscopically.

12. A method of maintaining a space between two adjacent vertebrae of a patient after removal of a disk from between the vertebrae comprising the steps of:

inserting a spacing device made at least partially from a shape-memory alloy having a transition temperature into the space between the two adjacent vertebrae after removal of the disk from between the two vertebrae at a temperature below the transition temperature of the shape-memory alloy; and allowing the spacing device to reach the transition temperature and a predetermined configuration suitable to its spacing function, the predetermined configuration having a height substantially equivalent to the space between the two adjacent vertebrae so that the space between the vertebrae is maintained.

13. A method of maintaining a space between two adjacent vertebrae of a patient after removal of a disk from between the vertebrae comprising the steps of:

inserting a spacing device made at least partially from a shape-memory alloy having a transition temperature into the space between the two adjacent vertebrae after removal of the disk from between the two vertebrae at a temperature below the transition temperature of the shape-memory alloy;

allowing the spacing device to reach the transition temperature and a predetermined configuration suitable to its spacing function; and configuring the spacing device to have a generally circular exterior profile when the spacing device is below the transition temperature of the shape-memory alloy and to have a generally rectangular profile when the spacing device is above the transition temperature of the shape-memory alloy.

14. Method of claim 13 further comprising the step of endoscopically introducing the spacing device into the space between the two adjacent vertebrae.

15. Method of claim 12 further comprising the step of providing the spacing device with teeth on an exterior surface of the spacing device.

16. Method of claim 12 further comprising the step of providing the spacing device with perforations to allow bony ingrowth.

* * * * *